(12) United States Patent
Zecchino et al.

(10) Patent No.: US 12,138,331 B2
(45) Date of Patent: Nov. 12, 2024

(54) FOAMING CLEANSER

(71) Applicants: Julius Zecchino, New York, NY (US);
Marina Turso, River Edge, NJ (US)

(72) Inventors: Julius Zecchino, New York, NY (US);
Marina Turso, River Edge, NJ (US)

( * ) Notice: Subject to any disclaimer, the term of this patent is extended or adjusted under 35 U.S.C. 154(b) by 0 days.

(21) Appl. No.: 17/875,236

(22) Filed: Jul. 27, 2022

(65) Prior Publication Data
US 2024/0033193 A1 Feb. 1, 2024

(51) Int. Cl.
| | |
|---|---|
| *A61K 8/04* | (2006.01) |
| *A61K 8/25* | (2006.01) |
| *A61K 8/29* | (2006.01) |
| *A61K 8/34* | (2006.01) |
| *A61K 8/36* | (2006.01) |
| *A61K 8/368* | (2006.01) |
| *A61K 8/37* | (2006.01) |
| *A61K 8/44* | (2006.01) |
| *A61K 8/46* | (2006.01) |
| *A61K 8/49* | (2006.01) |
| *A61K 8/60* | (2006.01) |
| *A61K 8/73* | (2006.01) |
| *A61K 8/81* | (2006.01) |
| *A61K 8/92* | (2006.01) |
| *A61Q 1/14* | (2006.01) |
| *A61Q 19/10* | (2006.01) |

(52) U.S. Cl.
CPC ............... *A61K 8/046* (2013.01); *A61K 8/25* (2013.01); *A61K 8/29* (2013.01); *A61K 8/345* (2013.01); *A61K 8/361* (2013.01); *A61K 8/368* (2013.01); *A61K 8/37* (2013.01); *A61K 8/447* (2013.01); *A61K 8/466* (2013.01); *A61K 8/4926* (2013.01); *A61K 8/494* (2013.01); *A61K 8/60* (2013.01); *A61K 8/73* (2013.01); *A61K 8/8147* (2013.01); *A61K 8/8158* (2013.01); *A61K 8/922* (2013.01); *A61Q 1/14* (2013.01); *A61Q 19/10* (2013.01); *A61K 2800/75* (2013.01)

(58) Field of Classification Search
CPC ..................................................... A61Q 19/10
See application file for complete search history.

(56) References Cited

U.S. PATENT DOCUMENTS

| | | | | |
|---|---|---|---|---|
| 7,279,454 B2 * | 10/2007 | Farooq | ................... | C11D 3/226 510/474 |
| 10,695,276 B2 * | 6/2020 | Yumioka | ................... | A61K 8/44 |
| 2006/0240122 A1 * | 10/2006 | Miner | ................... | C11D 3/222 424/618 |
| 2011/0044920 A1 * | 2/2011 | Hines | ................... | A61Q 19/00 424/195.17 |

FOREIGN PATENT DOCUMENTS

| | | | | |
|---|---|---|---|---|
| CN | 112274446 A | * | 1/2021 | |
| EP | 1396261 A1 | * | 3/2004 | ............. A61K 31/52 |
| EP | 2937075 A1 | * | 10/2015 | ............. A61K 8/14 |
| KR | 2010094055 A | * | 8/2010 | ............. A61K 8/345 |

* cited by examiner

*Primary Examiner* — Gina C Justice
(74) *Attorney, Agent, or Firm* — Dan De La Rosa

(57) ABSTRACT

A foaming skin cleanser formulation comprising silver, stearic acid, myristic acid, linoleic acid, propanediol, carbomer, polyquarternium-39, cocamidopropyl hydroxysultaine, pomegranate sterols (cholesterol), Coco-caprylate/caprate, *Cocos nucifera*, Sodium Cocoyl Isethionate, and mixtures and combinations thereof.

11 Claims, No Drawings

FOAMING CLEANSER

SUMMARY

The following implementations and aspects thereof are described and illustrated in conjunction with ingredients, formulations and methods that are meant to be exemplary and illustrative, not limiting in scope. The presently claimed invention relates to a cleanser that provides for high foaming, cleansing but does not strip the skin. The key to these results are based on the in-situation formation of soap with the addition of syndet. For purposes of this invention, the term "syndet" is a combination of the words "synergetic" and "detergent", and technically, it is the binding that occurs between different detergents, also known as surfactants or tension active agents. The formulation with the carbomer dispersed first and co-neutralized at the point of soap formation forms a stable matrix. These and other advantages will become apparent to those skilled in the relevant art upon a reading of the following descriptions.

In one embodiment a skin cleanser formulation comprising silver, stearic acid, myristic acid, linoleic acid, propanediol, carbomer, polyquarternium-39, cocamidopropyl hydroxysultaine, pomegranate sterols (cholesterol), Coco-caprylate/caprate, Cocos nucifera, Sodium Cocoyl Isethionate, and mixtures and combinations thereof.

In another embodiment a skin cleanser formulation comprising at least one cleansing agent and at least one barrier agent.

In a further embodiment a skin cleanser formulation wherein the cleansing agent is selected from group comprising of the soap formed from saponifying Potassium hydroxide with a fatty acid, Potassium stearate, potassium myristate, potassium palmitate, sucrose, caffeine, salicylic acids and mixtures and combinations thereof.

In still another embodiment a formulation wherein the barrier agent is selected from group comprising of linoleic acid, barley extract, pomegranate steroid, ceramides, Coco nucifera, Coco-caprylate/caprate, ceramides, lipids steals, niacinamide, horsedeum distichon barley, wheat germ and mixtures and combinations thereof.

In still a further embodiment a formulation further comprising an anti-irritant agent, thenanti-irritant agent is selected from group comprising of sucrose, caffeine, and mixtures and combinations thereof.

In yet a further embodiment a formulation further comprising a colorant, the colorant is selected from group comprising of titanium dioxide, calcium sodium borosilicsate, mica, iron oxides, dyes and titanate micas and mixtures and combinations thereof.

In yet another embodiment a formulation further comprising an anti-microbial agent, the anti-microbial agent is selected from group comprising of silver, and mixtures and combinations thereof.

In still a further embodiment a formulation further comprising a make-up removing agent, the make-up removing agent is selected from group comprising of propanediol, glycerin, butylenes, propylene glycols, sorbitol, and mixtures and combinations thereof.

In still another embodiment a formulation further comprising a foam stabilizing agent, the foam stabilizing agent is selected from group comprising of cocamidopropyl hydroxysultaine, carbomer, cocamido proryl betaine and mixtures and combinations thereof.

In yet a further embodiment a formulation further comprising a thickening agent, the thickening agent is selected from group comprising of carbomer, xanthan gum, hydroxy ethyl cellulose, veegum, bentonites, sodium polyacrylate and mixtures and combinations thereof.

In yet another embodiment a formulation further comprising a cationic skin softening agent, the cationic skin softening agent is selected from group comprising of polyquarternium-30, quad 40, quad 32, quad 33, squalene, amaranthus oil and mixtures and combinations thereof.

In still a further embodiment a formulation further comprising a moisturizing agent, the moisturizing agent is selected from group comprising of glycerine, polyglutamic acid, hyaluronic acid, and mixtures and combinations thereof.

In still another embodiment a formulation wherein the cleansing agent is from about 5% to about 50% of the formulation and said barrier agent is from about 0.2% to about 10% of said formulation.

In yet a further embodiment a formulation wherein the anti-irritant agent is from about % to about 5% of the formulation.

In yet another embodiment a formulation wherein said colorant is from about 0% to about 10% of the formulation.

In still a further embodiment a formulation wherein the anti-microbial agent is from about 0.2% to about 5.0% of the formulation.

In still another formulation of claim 8 wherein the make-up removing agent is from about 2% to about 20% of the formulation.

In yet a further embodiment a formulation of wherein the foam stabilizing agent is from about 0.2% to about 5% of the formulation.

In yet another embodiment a formulation wherein the thickening agent is from about 0.2% to about 5% of the formulation.

In still a further embodiment a formulation wherein the cationic skin softening agent is from about 0.1% to about 5% of the formulation.

In still another embodiment a formulation wherein the moisturizing agent is from about 0.2% to about 5% of the formulation.

In yet a further embodiment a skin cleanser formulation comprising silver, stearic acid, myristic acid, linoleic acid, propanediol, carbomer, polyquarternium-39, cocamidopropyl hydroxysultaine, pomegranate sterols (cholesterol), Coco-caprylate/caprate, Cocos nucifera, Sodium Cocoyl Isethionate, salicylic acid, sodium polyacrylate, niacinamide, polydextrose, caffeine and mixtures and combinations thereof.

In still a further embodiment, a formulation that provides for a dual function which contributes to both skin cleansing and skin moisturizing benefits.

DETAILED DESCRIPTION

As required, detailed embodiments of the present invention are disclosed herein; however, it is to be understood that the disclosed embodiments are merely exemplary of the invention that may be embodied in various forms. The figures are not necessarily to scale, some features may be exaggerated to show details of particular components. Therefore, specific structural and functional details disclosed herein are not to be interpreted as limiting, but merely as a basis for the claims and as a representative basis for teaching one skilled in the art to variously employ the present invention.

The present invention relates to multiple embodiments including the formulation set forth in Table 1. In one embodiment, the formulation comprises:

| Phase | Ingredients (INCI) | % |
|---|---|---|
| A | Water | 23.200 |
| A | Carbomer | 2.000 |
| B | Salicylic Acid & Sodium Polyacrylate & Niacinamide & Polydextrose & Caffeine | 8.000 |
| B | Water & Coconut Alkanes & Dicaprylyl Ether & Glycerin & Cocos Nucifera (Coconut) Water & Cocos Nucifera (Coconut) Fruit Juice & Coco-Caprylate/Caprate & Lecithin (from Sunflower) & Sodium Hyaluronate | 5.000 |
| C | Propanediol | 10.000 |
| C | Polyquaternium-39 | 1.000 |
| C | Sucrose | 1.000 |
| C | Caffeine | 0.100 |
| C | Bismuth Oxychloride & Ethylhexyl Hydroxystearate | 3.600 |
| C | Mica & Titanium Dioxide (CI 77891) | 1.050 |
| C | Calcium Sodium Borosilicate & Titanium Dioxide (CI 77891) & Ferric Ferrocyanide | 0.350 |
| D | Stearic Acid | 15.000 |
| D | Myristic Acid | 5.000 |
| D | Linoleic Acid | 0.200 |
| D | Punica Granatum (Pomegranate) Sterols | 0.500 |
| D | Squalane & Amaranthus Caudatus Seed Oil & Hordeum Distichon (Barley) Extract & Triticum Vulgare (Wheat) Germ Oil | 0.200 |
| E | Water & Potassium Hydroxide | 11.700 |
| F | Sodium Cocoyl Isethionate | 2.000 |
| G | Glycerin | 10.000 |
| G | Silver | 0.100 |
| | Formula Total: | 100.000 |

The first step is to admix water with carbomer to form Phase A. Then admix Propanediol, Polyquaternium-39, Cocamidopropyl Hydroxysultaine, Water & Coconut Alkanes & Dicaprylyl Ether & Glycerin & *Cocos nucifera* (Coconut) Oil & Propanediol & Olive Squalane & *Cocos Nucifera* (Coconut) Water & *Cocos nucifera* (Coconut), Fruit Juice & Coco-Caprylate/Caprate & Lecithin (from Sunflower) & Sodium Hyaluronate to form Phase B. After the formation of Phase B, admix Phase A with Phase B. Then admix Propanediol, Polyquaternium-39, Sucrose, Caffeine, Bismuth Oxychloride & Ethylhexyl Hydroxystearate, Mica & Titanium Dioxide (CI 77891), REFLECKS TRULY TURQUOISE (Calcium Sodium Borosilicate & Titanium Dioxide (CI 77891) & Ferric Ferrocyanide to form Phase C. After the combining the ingredients to form Phase C with the mixture of Phase A and B and heat below 100 degrees Celsius. Admix the ingredients of Phase D which includes Stearic Acid, Myristic Acid, Linoleic Acid, Punica Granatum (Pomegranate) Sterols & *Amaranthus Caudatus* Seed Oil & *Hordeum* Distichon (Barley) Extract & *Triticum Vulgare* (Wheat) Germ Oil to the mixture of Phase A, B and C for at least 10 minutes. Then admix water and potassium hydroxide to form Phase E and then slowly admix Phase E into the mixture of Phase A, B, C and D for at least 1 hour. Admix sodium cocoyl isethionate which is Phase F to the mixture of Phase A, B, C, D and E until uniform. Once uniform, start the cooling process. Then admix glycerin and silver to form Phase G and admix Phase G to the mixture until uniform and allow to cool to room temperature below at least 30 degrees Celsius.

In another embodiment, the present invention relates to the a skin care cleanser formulation with the ingredients set forth in Table 2. The formulation comprises:

| Phase | Ingredients | % |
|---|---|---|
| A | Water | 24.300 |
| A | Carbomer | 2.000 |
| B | Propanediol | 10.000 |
| B | Polyquaternium-39 | 1.000 |
| B | Cocamidopropyl Hydroxysultaine) | 8.000 |
| B | Water & Coconut Alkanes & Dicaprylyl Ether & Glycerin & Cocos Nucifera (Coconut) Oil & Propanediol & Olive Squalane & Cocos Nucifera (Coconut) Water & Cocos Nucifera (Coconut) Fruit Juice & Coco-Caprylate/Caprate & Lecithin (from Sunflower) & Sodium Hyaluronate | 5.000 |
| B | Sucrose | 1.000 |
| B | Caffeine | 0.100 |
| B | Bismuth Oxychloride & Ethylhexyl Hydroxystearate | 3.600 |
| B | Mica & Titanium Dioxide (CI 77891) | 1.050 |
| B | Calcium Sodium Borosilicate & Titanium Dioxide (CI 77891) & Ferric Ferrocyanide 0.350 Innospec PUREACT I-78 FLAKE Sodium Cocoyl Isethionate) | 2.000 |
| C | Stearic Acid | 15.000 |
| C | Myristic Acid | 5.000 |
| C | Linoleic Acid | 0.200 |
| C | Punica Granatum (Pomegranate) Sterols | 0.500 |
| C | Squalane & *Hordeum* Distichon (Barley) Extract & *Triticum Vulgare* (Wheat) Germ Oil | 0.200 |
| D | Water & Potassium Hydroxide | 10.600 |
| E | Glycerin | 10.000 |
| E | Silver | 0.100 |
| | Formula Total: | 100.000 |

The first step is to admix water with carbomer to form Phase A. Then admix Propanediol, Polyquaternium-39, Cocamidopropyl Hydroxysultaine, Water & Coconut Alkanes & Dicaprylyl Ether & Glycerin & *Cocos nucifera* (Coconut) Oil & Propanediol & Olive Squalane & *Cocos Nucifera* (Coconut) Water & *Cocos nucifera* (Coconut), Fruit Juice & Coco-Caprylate/Caprate & Lecithin (from Sunflower) & Sodium Hyaluronate, Propanediol, Polyquaternium-39, Sucrose, Caffeine, Bismuth Oxychloride & Ethylhexyl Hydroxystearate, Mica & Titanium Dioxide (CI 77891), REFLECKS TRULY TURQUOISE (Calcium Sodium Borosilicate & Titanium Dioxide (CI 77891) to form Phase B. After the formation of Phase B, admix Phase A with Phase B. Then admix Stearic Acid, Myristic Acid, Linoleic Acid, Punica Granatum (Pomegranate) Sterols & Squalane & *Hordeum* Distichon (Barley) Extract & *Triticum Vulgare* (Wheat) Germ Oil to form Phase C. After the combining the ingredients to form Phase C with the mixture of Phase A and B and heat below 100 degrees Celsius. Admix the ingredients of Phase C which includes to the mixture of Phase A, B and C for at least 10 minutes. Then admix water and potassium hydroxide to form Phase D and then slowly admix Phase E into the mixture of Phase A, B, C and D for at least 1 hour. Once uniform, start the cooling process. Then admix glycerin and silver to form Phase E and admix Phase E to the mixture until uniform and allow to cool to room temperature below at least 30 degrees Celsius.

Most, if not all, cleansing formulations have a propensity to dry the skin thereby causing numerous dermal problems. Thus, the end user is required to add an additional step by subsequently using a moisturizer to combat the dry skin problem. The presently claimed invention is unique because it provides skin cleansing with the moisturizing benefits at the levels of a moisturizing product.

Clinical testing was conducted on the present invention at Essex Labs to prove its dual function of skin cleansing and moisturizing benefits as set forth below.

The objectives of the study were to valuate the safety-in-use of the cleanser after 2 weeks, with pre- and post-test eye examinations being performed by a Board-Certified Ophthalmologist to support the claims "Ophthalmologist-Tested" and "Safe for Contact Lens Wearers"; determine the effect on skin barrier function (transepidermal water loss [TEWL]) of the cleanser after 2 weeks of use; determine the moisturization efficacy of the cleanser immediately after application and after 2 weeks of use; determine if the cleanser improved skin brightness after 2 weeks of use; and evaluate the consumer perception of the cleanser after 2 weeks of product use on a panel of 30 female volunteers between 35-69 years old, approximately 25% of whom were to be contact lens wearers.

The inclusion criteria for the study was as follows: a. Females between the ages of 35 and 69 years (inclusive) in general good health (no physical required); b. Individuals with a skin texture/roughness score of "5" or greater (moderately rough skin texture) on the face; c. Individuals with a skin brightness score of "5" or greater (moderately dull appearance) on the face; d. Individuals who indicated their willingness to participate in the study, follow directions and remain on the study for the entire 3-week test period; and e. Individuals who could read, understand and sign the Informed Consent Form; and f. Individuals who were regular users of face cleansers.

The study was designed as a 2-week study preceded by a 1-week washout period in which the test article was to be used by each of the test subjects according to the instructions. Subjects came to the Testing Facility to begin the washout phase. A trained technician visually evaluated skin texture and skin brightness/radiance on the face of each subject to determine qualification. If qualified, subjects filled out paperwork and were instructed to use Ivory soap for 1 week.

All subjects were instructed to return to the Testing Facility after 2 weeks of product use for additional digital photographs, instrumental measurements, irritation evaluations, and to answer a Sponsor-supplied questionnaire. A total of 31 female subjects ranging in age from 36 to 69 years and 11 of whom were contact lens wearers) were enrolled on Sep. 24, 2021. All 31 subjects completed the single blind, home-use test on Oct. 13, 2021. Subject demographics are presented in Appendix 1, Table 1. Daily diary comments are listed in Appendix 1. Table 2. Of the total subjects completing the study, 11 subjects were contact lens wearers, 11 wore glasses, and 9 had uncorrected vision.

Visual acuity examinations, made by a trained evaluator, were conducted at baseline (pre-test) and again after 2 weeks of test article use (post-use). There were no clinically relevant changes in the visual acuity of any test subject. There were no test article-related adverse effects observed by the examining Ophthalmologist at the 2-week post-use examination.

At baseline and after 2 weeks of product use, a trained technician measured harrier function on the face of each subject with the Tewameter®. The following table presents a summary of the Tewameter® measurements:

Tewameter ® Measurements Mean +− Standard Deviation (S.D.), Mean Change from Baseline and % of Subjects with Improvement Baseline

|  | Mean +− S.D. | p-value | Mean Change From Baseline | % of Subjects with improvement form Baseline |
| --- | --- | --- | --- | --- |
| Baseline | 14.04 +− 3.25 | — | — | — |
| 2 Weeks | 10.84* +− 3.52 | <0.001 | −22.8% | 94% |

When measurements taken after 2 weeks of product use were compared with baseline measurements, there was a mean improvement of 22.8%. The improvement was highly significant compared with baseline. A total of 94% of the subjects showed improvement after 2 weeks of product use.

At baseline, immediately after the first application, and after 2 weeks of product use, a trained technician measured skin moisture on the face of each subject with the Corneometer®. The following table presents a summary of the Corneometer® measurements:

Tewameter ® Measurements Mean +− Standard Deviation (S.D.), Mean Change from Baseline and % of Subjects with Improvement Baseline

|  | Mean +− S.D. | p-value | Mean Change From Baseline | % of Subjects with improvement form Baseline |
| --- | --- | --- | --- | --- |
| Baseline | 14.04 +− 3.25 | — | — | — |
| 2 Weeks | 10.84* +− 3.52 | <0.001 | −22.8% | 94% |

When measurements taken immediately after the first application and after 2 weeks of product use were compared with baseline measurements, there were mean improvements of 113% and 118%, respectively. The improvements were highly significant compared with baseline. All of the subjects showed improvement immediately after the first application and after 2 weeks of product use.

10.4 Irritation Evaluation

At baseline, immediately after the first application and after 2 weeks of use, a trained technician evaluated the face of each subject for irritation. There was no irritation observed during the study.

baseline and after 2 weeks of product use, a trained technician took digital images of the face of each subject with the Visia CR® imaging system. Using ImageProg® software, the images were analyzed to determine changes (if any) in the appearance of skin texture. A decrease in the score represents an improvement in the appearance of skin texture. Individual scores and the statistical analysis are presented in Appendix The following table presents a summary of the skin texture image analysis:

Skin Texture Evaluation - Image Analysis Mean Score +− S.D., Mean Change from Baseline

|  | Mean +− S.D. | p-value | Mean Change From Baseline | % of Subjects with improvement form Baseline |
| --- | --- | --- | --- | --- |
| Baseline | 247.1 +− 38.7 | — | — | — |
| 2 Weeks | 247.3 +− 43.0 | 0.774 | 0.1% | 45% |

When images taken after 2 weeks of product use were compared with baseline images, there was a mean worsening of 0.1% based on image analysis. The worsening observed after 2 weeks of use was not statistically significant compared with baseline. A total of 45% of the subjects showed improvement after 2 weeks of product use.

At baseline and after 2 weeks of product use, a trained technician took digital images of the face of each subject with the Visia CR® imaging system. Using ImagePro® software, the images were analyzed to determine changes (if any) in the appearance of skin brightness. An increase in the score represents an improvement in the appearance of skin brightness.

The following table presents a summary of the skin texture image analysis:

Skin Texture Evaluation - Image Analysis Mean Score +− S.D., Mean Change from Baseline

|  | Mean +− S.D. | p-value | Mean Change From Baseline | % of Subjects with improvement form Baseline |
|---|---|---|---|---|
| Baseline | 247.1 +− 38.7 | — | — | — |
| 2 Weeks | 247.3 +− 43.0 | 0.774 | 0.1% | 45% |

When images after 2 weeks of product use were compared with baseline images, there was a mean improvement of 1.8%, based on image analysis. The improvement observed after 2 weeks was statistically significant compared with baseline. A total of 74% of the subjects showed improvement after 2 weeks of product use.

After 2 weeks of product use, subjects were required to complete a questionnaire. The following table presents a summary of subject responses after 2 weeks of product use:

Questionnaire Response Summary - 2 Weeks

|  | Strongly Agree or Agree | Disagree or Strongly Disagree | Not Applicable |
|---|---|---|---|
| The cleanser's soft lather creates a gentle foam that rinses easily without stripping or drying | 100% | 0% |  |
| The cleanser removed all traces of makeup, excess oil, pollution, and other grime leaving the skin clean, soft and smooth and protected | 97% | 3% |  |
| After using the cleanser my skin looks and feels bright, refreshed, soft and supple. No dry after feel. | 100% | 0% |  |
| After using the cleanser for a short time, I notice maskne disappearing. | 74% | 13% | 13% |
| My skin felt clean with no irritation of dryness | 100% | 0% |  |
| The cleanser has a pleasant odor. | 94% | 6% |  |
| Are you familiar with silver has a skin protecting ingredient? | 0% | 100% |  |
| Would you recommend this product to a family member? | 100% | 0% |  |

A single-blind, home-use test was conducted with 31 female subjects (35% of whom were contact lens wearers) who used Test Article: BeautyStat Universal Microbiome Barrier Balancing Cleanser 8106-3156.63 21-537 twice daily for 2 weeks. Test Article: was the applied for invention referred to as BeautyStat Universal Microbiome Barrier Balancing Cleanser 8106-3156.63 21-537 was found to be safe for use near the eye area and the claims "Ophthalmologist-Tested" and "Safe for Contact Lens Wearers" are considered to be supported.

Skin barrier function was significantly improved after 2 weeks of use, based on Tewameter® measurements, Skin moisture was significantly improved immediately after the first application and after 2 weeks of use, based on Corneometer® measurements. There was no irritation, Observed during the study. Skin brightness was significantly improved after 2 weeks of use, based on image analysis. After 2 weeks of use, the product was associated with a high level of acceptance, with subjects responding very favorably to all of the questions regarding product performance.

Numerous modifications and variations of the present invention are possible in light of the above teachings. It is therefore to be understood that within the scope of the attendant claims attached hereto, this invention may be practiced otherwise than as specifically disclosed herein.

What is claimed is:

1. A skin cleanser formulation consisting of silver, stearic acid, myristic acid, linoleic acid, propanediol, carbomer, polyquarternium-39, cocamidopropyl hydroxysultaine, pomegranate sterols, coco-caprylate/caprate, *Cocos nucifera*, and sodium cocoyl isethionate.

2. A skin cleanser formulation consisting of at least one cleansing agent, and at least one barrier agent, at least one anti-irritant agent, at least one colorant, at least one anti-microbial agent, at least one make-up removing agent, at least one foam stabilizing agent, at least one thickening agent, at least one cationic skin softening agent, and at least one moisturizing agent, said at least one cleansing agent is selected from the group consisting of the soap formed from saponifying potassium hydroxide with a fatty acid, potassium stearate, potassium myristate, potassium palmitate, sucrose, caffeine, salicylic acids and mixtures and combinations thereof, said at least one barrier agent is selected from the group consisting of linoleic acid, barley extract, pomegranate sterols, ceramides, *Cocos nucifera*, coco-caprylate/caprate, lipids sterols, niacinamide, wheat germ oil and mixtures and combinations thereof, said at least one anti-irritant agent is selected from the group consisting of sucrose, caffeine, and mixtures and combinations thereof, said at least one colorant is selected from the group consisting of titanium dioxide, calcium sodium borosilicsate, mica, iron oxides, dyes and titanate micas and mixtures and combinations thereof, said at least one anti-microbial agent is silver, said at least one make-up removing agent is selected from the group consisting of propanediol, glycerin, butylenes, propylene glycols, sorbitol, and mixtures and combinations thereof, said at least one foam stabilizing agent is selected from the group consisting of cocamidopropyl hydroxysultaine, carbomer, cocamido proryl betaine and mixtures and combinations thereof, said at least one thickening agent is selected from group comprising of carbomer, xanthan gum, hydroxy ethyl cellulose, veegum, bentonites, sodium polyacrylate and mixtures and combinations thereof, said at least one cationic skin softening agent is selected from the group consisting of polyquarternium-30, quarternium-40, quarternium-32, quarternium-33, squalene, *amaranthus* oil and mixtures and combinations thereof, and said at least one moisturizing agent is selected from the group consisting of glycerine, polyglutamic acid, hyaluronic acid, and mixtures and combinations thereof.

3. The formulation of claim 2 wherein said at least one cleansing agent is from about 5% to about 50% of said formulation and said barrier agent is from about 0.2% to about 10% of said formulation.

4. The formulation of claim 2 wherein said at least one anti-irritant agent is from about 0.05% to about 5% of said formulation.

5. The formulation of claim 2 wherein said at least one colorant is from about 0.1% to about 10% of said formulation.

6. The formulation of claim 2 wherein said at least one anti-microbial agent is from about 0.2% to about 5.0% of said formulation.

7. The formulation of claim 2 wherein said at least one make-up removing agent is from about 2% to about 20% of said formulation.

8. The formulation of claim 2 wherein said at least one foam stabilizing agent is from about 0.2% to about 5% of said formulation.

9. The formulation of claim 2 wherein said at least one thickening agent is from about 0.2% to about 5% of said formulation.

10. The formulation of claim 2 wherein said at least one cationic skin softening agent is from about 0.1% to about 5% of said formulation.

11. The formulation of claim 2 wherein said at least one moisturizing agent is from about 0.2% to about 5% of said formulation.

* * * * *